United States Patent [19]

Ishikawa et al.

[11] Patent Number: 4,578,222

[45] Date of Patent: Mar. 25, 1986

[54] PROCESS FOR PREPARING A PERFLUORINATED OR POLYFLUORINATED ALIPHATIC CARBOXYLIC ACID

[75] Inventors: Nobuo Ishikawa, Yokohama; Mitsuru Takahashi, Tokyo, both of Japan

[73] Assignees: Daikin Kogyo Co., Ltd., Yamaguchi; Toyo Soda Manufacturing Co., Ltd., Osaka, both of Japan

[21] Appl. No.: 762,228

[22] Filed: Aug. 5, 1985

Related U.S. Application Data

[63] Continuation of Ser. No. 566,115, Dec. 27, 1983, abandoned.

[30] Foreign Application Priority Data

Dec. 31, 1982 [JP] Japan .................................. 57-233997

[51] Int. Cl.$^4$ ....................... C07C 51/15; C07G 13/00
[52] U.S. Cl. ................................ 260/413; 204/157.62; 562/550
[58] Field of Search ..................... 562/550; 260/413 R; 204/158 S

[56] References Cited

U.S. PATENT DOCUMENTS

| 3,311,657 | 3/1967 | Graham | 562/550 |
| 3,542,859 | 11/1970 | Litt et al. | 562/550 |
| 3,706,809 | 12/1972 | Moroe et al. | 568/878 |
| 3,711,560 | 1/1973 | Ramsden | 568/878 |
| 4,034,000 | 7/1977 | Schoenberg | 568/857 |
| 4,098,806 | 7/1978 | Commeyras et al. | 562/550 |
| 4,221,734 | 9/1980 | Commeyras et al. | 562/550 |
| 4,466,870 | 8/1984 | Boudjouk et al. | 204/158 S |

FOREIGN PATENT DOCUMENTS 53813  4/1977  Japan ................................. 562/550

*Primary Examiner*—J. E. Evans
*Attorney, Agent, or Firm*—Armstrong, Nikaido, Marmelstein & Kubovcik

[57] ABSTRACT

A process for preparing a perfluorinated or polyfluorinated aliphatic carboxylic acids wherein a perfluorinated or polyfluorinated aliphatic halide of the formula: $R_fX$ where $R_f$ is a perfluorinated or polyfluorinated aliphatic group and X is a halogen atom is reacted with carbon dioxide in the presence of metal under the irradiation of ultrasound and the reaction product is hydrolyzed to form a perfluorinated or polyfluorinated aliphatic carboxylic acid of the formula: $R_fCOOH$ where $R_f$ is the same as defined above.

7 Claims, No Drawings

PROCESS FOR PREPARING A PERFLUORINATED OR POLYFLUORINATED ALIPHATIC CARBOXYLIC ACID

This is a continuation of application Ser. No. 566,115 filed Dec. 27, 1983, now abandoned.

BACKGROUND OF THE INVENTION

1. Field of the Invention

This invention relates to a process for preparing a perfluorinated or polyfluorinated aliphatic carboxylic acid that is useful particularly because of their chemical and/or physiological properties.

2. Description of the Prior Art

For the process for preparation of a perfluoroalkyl carboxylic acid from a perfluoroalkyl iodide and carbon dioxide ($CO_2$), a formerly known method makes use of zinc other metal pair (Japanese Patent Opening Nos. 106808/1977 and 77008/1977). However, this method needs preparation of the metal pair and it is difficult to perform the preparation with good reproducability. Further, the procedure for the reaction is not simple and the yield of the target product is low. A method to make use of an unactivated zinc powder in a similar reaction system has also been disclosed but it is described to yield only a little reaction product of perfluoroalkyl iodide with carbon dioxide gas, the conversion rate, for example, never exceed 7% in case the perfluoroalkyl group contains six carbon atoms. Therefore, also this second method cannot be adapted to be efficient for industrial synthesis.

OBJECTS AND SUMMARY OF THE INVENTION

Accordingly, it is an object of the present invention to provide a process of synthesis that is capable of producing perfluorinated or polyfluorinated aliphatic carboxylic acid in high yield.

Namely, this invention provides a process for preparing a perfluorinated or polyfluorinated aliphatic carboxylic acid wherein a perfluorinated or polyfluorinated aliphatic halide of the formula: $R_fX$ where $R_f$ is a perfluorinated or polyfluorinated aliphatic group and X is a halogen atom, for example, chlorine, bromine or iodine, is reacted with carbon dioxide in the presence of metal under the irradiation of ultrasound, thus obtained product being hydrolyzed to give a perfluorinated or polyfluorinated aliphatic carboxylic acid of the formula: $R_fCOOH$ where $R_f$ is the same as defined above.

Other and further objects, features and advantages of the invention will appear more fully from the following description.

DESCRIPTION OF THE PREFERRED EMBODIMENT

The process of this invention is characterized by a reaction of a starting material $R_fX$ and carbon dioxide ($CO_2$) in the presence of metal under the action of ultrasound. It provides a simple or stable process to produce the target product without difficulty, perfluorinated or polyfluorinated aliphatic carboxylic acid in high yield. For example, in case the perfluorinated or polyfluorinated aliphatic halide used is $R_fI$ and zinc powder is used for the metal, the above reaction probably proceeds in the following reaction formula:

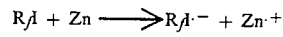
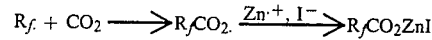
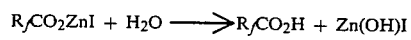

In this case, first, zinc metal affords a single electron to the reactants, particularly to $R_fI$ providing a radical anion $R_fI^-$. This unstable species collapse instantly to give $R_f$· radical, which is introduced together with $CO_2$ into a cavity formed by the ultrasound. At the next moment, the decavitation accompanying a high pressure assists the reaction between $R_f$· and $CO_2$ to form $R_fCO_2$·, which follows the reaction shown above.

The perfluorinated or polyfluorinated aliphatic halide ($R_fX$) used by the process of the invention is preferably one of the compounds of the following general formulas:

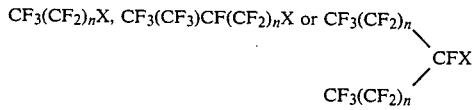

where X is a chlorine, bromine or iodine atom, n represents 0, 1 or a higher integer. Representative examples of such compounds are $CF_3I$, $CF_3CF_2I$, $CF_3(CF_2)_2I$, $CF_3(CF_2)_3I$, $CF_3(CF_2)_4I$, $CF_3(CF_2)_5I$, $(CF_3)_2CFI$, $(CF_3)_2CFCF_2I$, $(CF_3)_2CF(CF_2)_2I$, $(CF_3)_2CF(CF_2)_3I$, etc. Beside the above alkyl halide, aliphatic halide containing an unsaturated group, for example, $CF_2=CF-CF_2X$, $CF_3-CF=CFX$, etc. may be used. Examples are $CF_2=CF-CF_2I$ and $CF_3-CF=CFI$. However, the perfluorinated or polyfluorinated aliphatic halide used preferably contains not more than twenty carbon atoms in consideration of their solubility in solvent. The above perfluorinated or polyfluorinated aliphatic halide is not limited to the perfluorinated or polyfluorinated alkyl or alkenyl halide, and it may be a compound with a hydrogen atom or atoms bonded to part of its molecular chain, for example, $CF_3CF_2CH_2CF_2X$. Further, halides as expressed by a general formula: $X(CF_2CF_2)_nX$, for example, $I(CF_2CF_2)_nI$ can also be used. Beside, aliphatic halides having an aromatic substituent or substituents, for example, $C_6H_5-CF_2X$, $C_6H_5-(CF_2)_2X$, etc. may be used for the $R_fX$ as mentioned above.

The metal (hereinafter often abbreviated "M") used by the process of the invention may generally be any metal that can oxidatively add to $R_fX$ to form $R_fMX$. Among these, zinc and/or manganese is particularly preferable. These metals, zinc and manganese can be applied in the commercially available powdery form, which are preferably used in an amount ranging from 1 to 3 equivalents relative to $R_fX$. Particularly, the manganese can be used in the form of zero-valent manganese that is prepared from equivalent amounts of a manganous halide as expressed by a general formula: $MnX_2$ where X represents a chlorine, bromine or iodine atom and zinc powder in an aprotic polar solvent under the irradiation of ultrasound. Also in this case, it is preferable that 1 to 3 equivalents of Mn(O) to $R_fX$ is used for the process.

The above reaction to produce perfluorinated or polyfluorinated aliphatic carboxylic acid can be conducted in a wide temperature range. Normally, it can be designed to proceed satisfactorily at a moderate temperature (room temperature, preferably 20° C. to 100° C.) under the atmospheric pressure and in case of an experiment of small scale the ultrasound to be applied can be generated by a ultrasonic cleaner (28 to 200 W, 28 to 50 kHz) that is available commercially. Normally, the temperature of the water bath of such cleaner (as high as 60° C.) under the action of ultrasound is cooled but cooling is not always necessary.

In the reaction, an amount of carbon dioxide almost one equivalent to $R_fX$ is sufficient though a substantially excess amount of carbon dioxide may be used.

In the reaction, any solvent that is ordinarily used for a reactions with organometallic compound is applicable. An aprotic polar solvent is preferable, for which dimethylformamide, tetrahydrofuran, dimethylsulfoxide, dimethylacetamide, N-methylpyrrolidone, acetonitrile, sulfolane, etc. may be favorably used. Since having a high solvation energy with cationic ions, such polar solvent exhibits a high dissolving power, so it has an effect in increasing the rate of reaction with anionic reagents, facilitating, in the above reaction, the formation of the intermediate product (organometallic derivative) and the reaction of such intermediate product with carbon dioxide.

In the reaction, hydrolysis for producing a fluorine-containing aliphatic carboxylic acid (namely, perfluorinated or polyfluorinated aliphatic carboxylic acid) can be achieved using one of the ordinary mineral acids, for example, hydrochloric acid, sulfuric acid, or the like.

As mentioned above, the process of the invention combines the effect of ultrasound with the characteristic chemical property of perfluorinated or polyfluorinated aliphatic group to allow use of a commercially available zinc or manganese powder or the like without any further purification for production of a perfluorinated or polyfluorinated aliphatic carboxylic acid of high purity in a high yield. Further, the reaction proceeds under a moderate condition and the whole reaction can be conducted in a single vessel, simplifying the procedure of the reaction. Further, the solvent to be used needs no purification. For example, just drying on molecular sieve will give a satisfactory result.

Perfluorinated or polyfluorinated aliphatic carboxylic acid prepared by the porcess of the invention are useful compounds for use as surfactants, water/oil repellents, medicines, agricultural chemicals or as intermediates for the production thereof. Further, they are also useful intermediates for the production of monomers from which fluorine containing polymers are prepared.

The invention will be more clearly understood with reference to the following examples. However, these examples are intended to illustrate the invention and are not to be construed to limit the scope of the invention with various changes possible within the scope of the claims without departing from the spirit of the invention.

EXAMPLE 1

To a 50 ml round-bottomed flask fitted with a gas introducing tube, were added 1.30 g (0.02 gram-atom) of commercially available zinc powder, and 5.5 g (10 mmol) of $C_8F_{17}I$ and 20 ml of dimethylformamide that was dried on molecular sieve. $CO_2$ gas was introduced at a flow rate of 5 ml/min to the solution in a water bath for two hours with appling the action of ultrasound by a commercially available ultrasonic cleaner (45 KHz, 35 W). After the reaction, 100 ml of 1N HCl was added for hydrolysis. The oily layer thus produced was subjected to extraction with diethyl ether. The solvent was evaporated to dryness and the residue (NMR yield of 84% by a measurement using trifluoromethylbenzene as the internal standard) were dissolved in 150 ml of 1N NaOH. Conc. HCl was then added to lower the pH to not more than 2. The solution was extracted and the extract was dried on anhydrous magnesium sulfate and the solvent was evaporated. The residue was recrystallized from $CCl_4$. In the above procedure, it is supposed that a complex of dimethylformamide and the product (perfluorocarboxylic acid) is decomposed by the addition of NaOH, and a complex of dimethylformamide and HCl formed by the subsequent addition of HCl is transferred to an aqueous phase, and further the perfluorocarboxylic acid contained in the aqueous phase is transferred to an ether phase at the extraction with ether.

The resultant product, white crystal of $C_8F_{17}COOH$ having a melting point of 69 to 71° C. was produced in a yield of 72% (3.3 g). The product was identified by $^{19}F$ NMR spectroscopy, IR spectroscopy, and elementary analysis, which gave the following results:

$^{19}F$ NMR [$\delta$(ppm), external standard $CF_3COOH$, 56.45 MHz]: $\delta$4.8 (3F, t, J=10.4 Hz), 41 (2F, m), 44 (10F, m), 49.0 (2F, m);

IR (neat): $\nu_{C=O}$ 1775 cm$^{-1}$;

Elementary analysis:

Found: C: 23.29%, H: 0.22%.

Calcd.: C: 22.77%, H: 0.27%.

EXAMPLE 2

The same procedure and condition as Example 1 was applied for the reaction except for the use of 20 ml of dimethylsulfoxide as a reaction solvent, which gave $C_8F_{17}COOH$ in a yield of 57%.

EXAMPLE 3

To a 50 ml round-bottomed flask, were added 1.0 g (15 mg-atom) of commercially available zinc powder, 1.9 g (15 mmol) of $MnCL_2$ and 15 ml of dimethylformamide. Ultrasound generated in the same way as in Example 1 was applied for 1 hr to the solution to prepare zero-valent manganese. Next, a solution of 6 g (11 mmol) of $C_8F_{17}I$ in 5 ml of dimethylformamide was added. As in Example 1, $CO_2$ gas was introduced at a flow rate of 5 ml/min to the solution in a water bath for two hours under the irradiation of ultrasound by a ultrasonic cleaner (45 kHz, 35 W). The reaction was followed by the hydrolysis and then by the recrystallization such as in Example 1. 2.4 g (yield: 46%) of $C_8F_{17}COOH$ was thus produced.

EXAMPLE 4

The same procedure and condition as Example 3 were used for the reaction except for use of 20 ml of dimethylsulfoxide, which resulted in production of $C_8F_{17}COOH$ in a yield of 26%.

EXAMPLE 5

The same procedure and condition as Example 1 were used for the reaction except for use of 4.5 g (10.1 mmol) of $C_6F_{13}I$ as a starting material. To the residues that were obtained after a treatment with hydrochloric acid, 4.7 mmol of trifluoromethylbenzene was added as the internal standard, when the yield of $C_6F_{13}COOH$ was 77%. The product was further purified by distillation to get $C_6F_{13}COOH$ having a boiling point of 105° C./40 mmHg in a yield of 50%. The analytical data of this product were:

$^{19}F$ NMR [as in Example 1]: δ4.5 (3F, m), 41.0 (2F, m), 44.0 (2F, m), 45.5 (4F, m), 48.8 (2F, m);

IR (neat): $\nu_{C=O}$ 1775 cm$^{-1}$.

EXAMPLE 6

The same procedure and condition as Example 1 was applied for the reaction except for use of 3.49 g (10 mmol) of $C_4F_9I$. A NMR yield was 61% using trifluoromethylbenzene as the internal standard. The product was purified by distillation, which gave $C_4F_9COOH$ having a boiling point of 70° C./40 mmHg. The analytical data with this product were:

$^{19}F$ NMR [as in Example 1]: δ4.5 (3F, tt, J=8.5, 2.3 Hz), 41.3 (2F, tq, J=8.5, 1.9 Hz), 45.8 (2F, m), 48.3 (2F, m);

IR (neat): $\nu_{C=O}$ 1775 cm$^{-1}$.

EXAMPLE 7

The same procedure and condition as Example 1 was applied for the reaction except for use of 5 g (7 mmol) of $C_3F_7I$. A NMR yield was 48% using trifluoromethylbenzene as the internal standard. The product was purified by distillation, which gave $(CF_3)_2CFCOOH$ having a boiling point of 65° C./47 mmHg in a yield of 42%. The analytical data of this product were:

$^{19}F$ NMR [as in Example 1]: δ−2.0 (6F, d, J=6.6 Hz), 102.5 (1F, Sep, J=6.6 Hz);

$^1H$ NMR [TMS in $CCl_4$, 90 MHz]: δ11.0 (s, —COOH);

IR (neat): $\nu_{C=O}$ 1760 cm$^{-1}$.

EXAMPLE 8

The same procedure and condition as Example 1 was used for the reaction except for use of 5 g of $C_8F_{17}Br$ instead of $C_8F_{17}I$. 2.4 g (yield: 52%) of $C_8F_{17}COOH$ was thus produced.

EXAMPLE 9

The same procedure and condition as Example 1 was used for the reaction except for use of 3 g of $C_4F_9BR$ instead of $C_8F_{17}I$. 1 g (yield: 36%) of $C_4F_9COOH$ was thus produced.

What is claimed is:

1. A process for preparing a perfluorinated or polyfluorinated aliphatic carboxylic acid comprising reacting a perfluorinated or polyfluorinated aliphatic halide of the formula $R_fX$, where $R_f$ is a perfluorinated or polyfluorinated aliphatic group and X is a halogen atom, with carbon dioxide in the presence of zinc powder under the action of ultrasound and hydrolyzing the obtained product to form a perfluorinated or polyfluorinated aliphatic carboxylic acid of the formula: $R_fCOOH$ where $R_f$ is the same as defined above.

2. A process as claimed in claim 1 wherein $R_f$ is a perfluorinated or polyfluorinated aliphatic group of straight or branched chain that may be saturated or unsaturated, the number of carbon atoms being 1 to 20.

3. A process as claimed in claim 1 wherein said halogen atom X is a chlorine, bromine or iodine atom.

4. A process as claimed in claim 3 wherein said perfluorinated or polyfluorinated aliphatic halide is a perfluorinated or polyfluorinated alkyl iodide.

5. A process as claimed in claim 1 wherein an aprotic polar solvent is used as a reaction medium.

6. A process as claimed in claim 1 wherein said zinc powder is used in an amount of 1 to 3 equivalents relative to said perfluorinated or polyfluorinated aliphatic halide.

7. A process as claimed in claim 1 wherein the ambient temperature and atmospheric pressure is used.

* * * * *

UNITED STATES PATENT AND TRADEMARK OFFICE
CERTIFICATE OF CORRECTION

PATENT NO. : 4,578,222

DATED : March 25, 1986

INVENTOR(S) : Nobuo ISHIKAWA et al

It is certified that error appears in the above-identified patent and that said Letters Patent is hereby corrected as shown below:

On the cover page, Item [73] should read --Daikin Kogyo Co., Ltd., Osaka; Toyo Soda Manufacturing Co., Ltd., Yamaguchi, both of Japan--.

Signed and Sealed this

Seventh Day of October, 1986

[SEAL]

*Attest:*

DONALD J. QUIGG

*Attesting Officer*     *Commissioner of Patents and Trademarks*